United States Patent [19]
Roumagnac et al.

[11] Patent Number: 5,437,846
[45] Date of Patent: Aug. 1, 1995

[54] SYSTEM FOR SUPPORTING OBJECTS INSIDE A ROTATING DRUM

[75] Inventors: Jean-Patrick Roumagnac, Le Coteau; Francisco Naveros, Roanne; Jacques Timmermans, Perreux le Coteau, all of France

[73] Assignee: Barriquand Steriflow, Roanne, France

[21] Appl. No.: 196,193

[22] Filed: Feb. 22, 1994

[30] Foreign Application Priority Data

Aug. 30, 1991 [FR] France ................... 91 10802

[51] Int. Cl.⁶ .................................. A61L 2/00
[52] U.S. Cl. .................... 422/297; 414/766; 414/917; 422/292; 422/300; 422/302; 422/307
[58] Field of Search .......... 422/292, 295, 297, 300, 422/302, 303, 307, 309; 414/917, 766, 363, 360, 372

[56] References Cited

U.S. PATENT DOCUMENTS

| | | | |
|---|---|---|---|
| 2,277,310 | 3/1942 | Engelhart | 414/766 |
| 2,629,312 | 2/1953 | Davis . | |
| 3,895,911 | 7/1975 | Prins | 422/297 X |
| 4,228,134 | 10/1980 | Alfio | 422/208 |
| 5,201,234 | 4/1993 | Gull | 414/917 X |

FOREIGN PATENT DOCUMENTS 1935925  2/1971  Germany .................. 414/766

*Primary Examiner*—Robert J. Warden
*Assistant Examiner*—Krisanne M. Thornton
*Attorney, Agent, or Firm*—Poms, Smith, Lande & Rose

[57] ABSTRACT

The invention relates to a system for supporting objects inside a rotating drum, particularly in a sterilizer. The drum disposed in the enclosure rotates about the axis XX'. The supporting apparatus includes pressure plates, the displacements of which are controlled by pairs of levers disposed in the lateral parts of the drum, on either side of the stacks of objects. The levers pivot about pins under the action of controlling apparatus which may be actuators.

13 Claims, 3 Drawing Sheets

SYSTEM FOR SUPPORTING OBJECTS INSIDE A ROTATING DRUM

FIELD OF THE INVENTION

The present invention provides a system for supporting objects inside a rotating drum.

More precisely, the invention relates to a system which allows the support of objects stacked inside the rotating drum of apparatus such as a steriliser, an autoclave or the like.

BACKGROUND OF THE INVENTION

In the food or pharmaceutical industries, products or objects such as cans, jars, dishes, bottles, etc. are often sterilized in discontinuous or "batch" autoclaves into which the products to be treated are inserted, the products then being removed after completion of a specified treatment cycle. Such products to be treated are arranged in baskets, on stackable trays, or on other similar storage elements. For certain products, the sterilisation heat treatment should be carried out whilst the product is being stirred inside its packaging. Such stirring is produced inside the autoclave by rotating a drum housing baskets filled with packages containing the products to be sterilised. The same type of problem is posed when certain products are to be drained or tipped up in apparatus other than an autoclave, such apparatus therefore being called a drainer or tipper. This operation allows water deposited on the products to be removed by gravity during sterilisation.

An example of such a rotating drum sterilisation autoclave is described in detail in French patent no. 8602046.

As the drum rotates, it is necessary to avoid any movement of the packages which could cause them to be damaged or destroyed, by immobilizing the packages inside the drum using a specific supporting system. The individual product packages are usually stacked in boxes or placed in trays or racks, and it is the set of these boxes or similar which must be supported inside the drum.

To simplify the following description and claims, any package of a product to be sterilized will be designated generally as an "object".

In order to keep objects stacked inside a rotating drum in place, it has already been proposed, as in French patent application FR-A-2 605 226, to control the support plates for the objects by means of single-acting actuators disposed in the upper part of the drum and acting perpendicularly on the support plates. Such a solution certainly allows the objects to be held inside the drum without manual intervention, but it is unsatisfactory insofar as the single-acting actuators require associated return springs to allow removal of the support plates. Moreover, the actuator rods are connected directly to the presser plates, thereby limiting their stroke and requiring the use of actuators of a particular type because of the lack of space.

It has also been proposed in U.S. Pat. No. 2,629,312 to support objects inside a rotating drum using mechanisms for moving a presser plate, such a mechanism being manually operated by means of a handle and being disposed in the top of the drum. That solution is less than satisfactory insofar as the environment in which intervention is required is hostile, and insofar as manual intervention does not permit an automatic object treatment line to be set up.

Moreover, and most significantly, in all the proposed solutions, the mechanisms for pressing the plates are disposed in the upper part of the drum. That solution permits only limited travel of the plate and also, because of the small space available, does not allow the plates to be uniformly clamped.

OBJECTS AND SUMMARY OF THE INVENTION

To remedy the disadvantages mentioned above, an object of the invention is to provide a system for supporting objects stacked in a rotating drum, particularly in a sterilizer or similar apparatus, which system allows efficient automatic pressing to be spread equally over all the stacks of objects, and also fits better in the spaces available between the wall of the drum and the stacks of objects to be sterilized.

To achieve this object, the system for supporting at least one stack of objects inside a rotating drum, said drum comprising a floor to receive said stack, comprises at least one presser plate for application against the top part of said stack and means for displacing said plate so as to effectively apply it against said stack, wherein the displacement means comprise at least one member forming a lever disposed on at least one side of said stack, and pivotally mounted about a pin which is integral with said drum, parallel to said floor and perpendicular to the axis of rotation of said drum, and means for controlling the pivoting of said lever about its pin, said control means also being disposed on one side of said stack, a first end of the lever being driven by the control means and a second end being integral with said plate, displacement of the first end of the lever in a first direction causing the second end to approach said stack, whereby the plate is applied against the upper end of said stack.

In a preferred embodiment of the invention, the drum contains a plurality of stacks of objects and comprises, for each stack of objects, two pairs of identical levers, each pair being disposed on one side of said stack, said displacement control means applying to the first ends of the levers of each pair, a displacement which is independent of that which is applied to another pair, whereby the clamping of each plate associated with each stack of objects is achieved independently of the other plates.

According to a first embodiment of the invention, the pivoting of the levers is controlled by means of pneumatic or hydraulic actuators, each actuator controlling one pair of levers.

In a second embodiment of the invention, the displacements of the first ends of the levers are achieved by mechanical systems, such as screw-nuts for example, resilient systems being preferably interposed so as to ensure independent control of each pair of levers.

BRIEF DESCRIPTION OF THE DRAWINGS

Other features of the present invention will be seen more clearly from the following description of several embodiments of the invention which are given purely by way of non-limiting example. The description makes reference to the accompanying drawings in which.

MORE DETAILED DESCRIPTION

Figure 1:
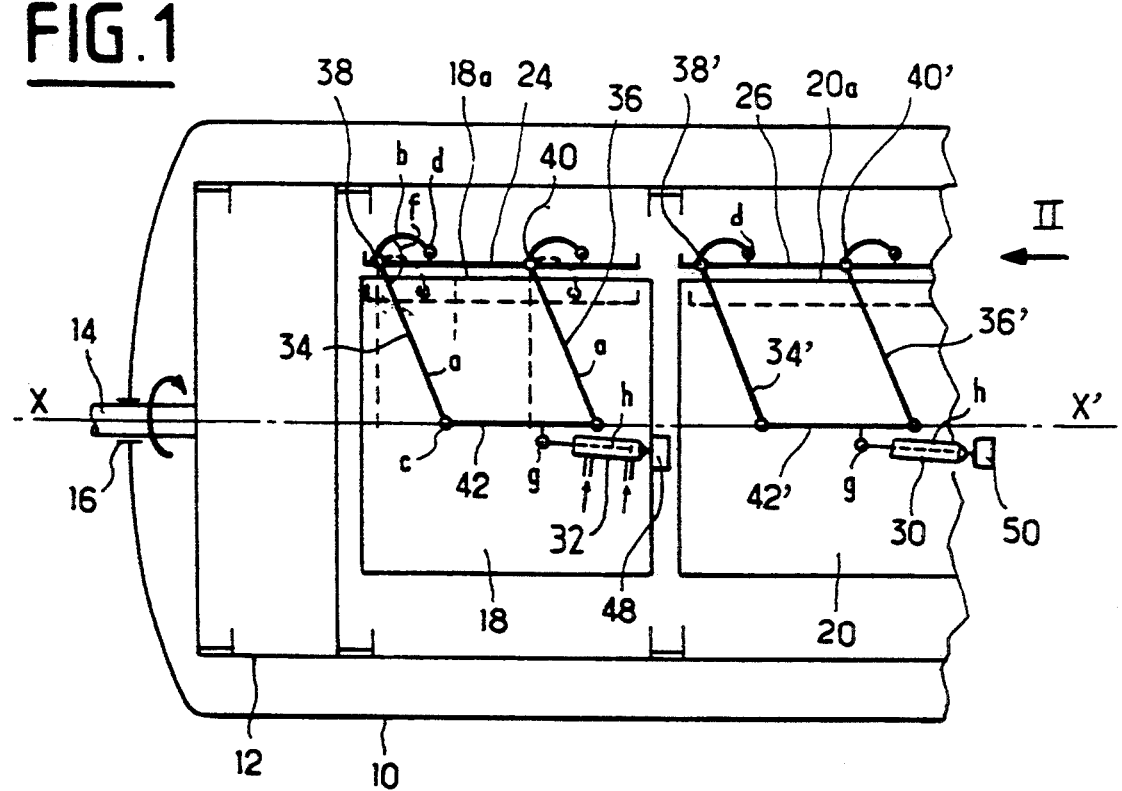
FIG. 1 is a vertical section view of a first embodiment of the support system controlled by means of an actuator.
Figure 2:
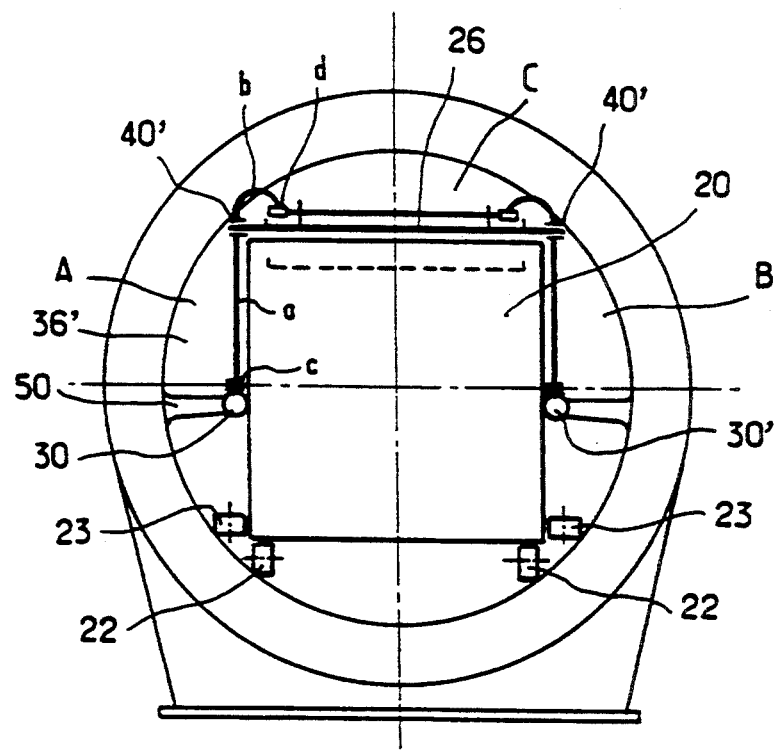
FIG. 2 is a view from the side along arrow II of FIG. 1.

Referring firstly to FIGS. 1 and 2, a first embodiment of the support system will be described, which comprises a control implemented by a pneumatic or hydraulic actuator.

These figures represent schematically the external pressure-resistant enclosure 10 of the autoclave which is closed by a cover (not shown) and, inside the enclosure 10, the rotating drum 12 which is mounted for rotation about the axis XX'. A portion of the shaft 14 which passes through the bearing 16 of the external enclosure 10 is shown in a simplified manner, this shaft allowing the drum 12 to be rotated about its axis XX'. Two stacks of objects 18 and 20 are represented symbolically by rectangles inside the drum 12. As seen more clearly in FIG. 2, the lower part of stack 20 rests on a series of rollers 22 which constitute a floor of the drum 12 and which facilitate introduction of the stacks of objects into the drum. Moreover, wheels such as 23 provide centering and lateral support for the stacks 18 inside the drum. As is well known the stacks of objects 18 and 20 are held against the floor by presser plates 24 and 26. In the rest position, the plates 24 and 26 are raised to allow the stacks of objects to be inserted without hindrance, whereas in the operating position, the plates are pressed against the upper portions 18a, 20a of the stacks of objects.

As previously indicated, according to an essential feature of the invention, the object support system which allows control of the displacements of the presser plates 24 and 26 between their rest positions and their operating positions is disposed on both sides of the stacks of objects, i.e. in the lateral zones A and B of the drum 12. Each presser plate is controlled by a pneumatic actuator 30, 30' for plate 26 and a pneumatic actuator (only a portion of which is shown in FIG. 1 and identified by the numeral 32) for plate 24, each actuator being disposed in one of the lateral zones A and B of the drum. The actuator 32 is connected to the corresponding plate 24 by a pair of levers with reference numerals 34 and 36. A similar pair of levers is situated on the other side of the stacks of objects 18 and 20. Each lever is pivotally mounted about a pin, the pins being 38, 40 for the levers 34 and 36, and 38', 40' for the levers 34' and 36' associated with the stack of objects 20. Each lever comprises a first arm a which extends from the associated hinge pin up to a second end c. Each lever also comprises a slightly bent second arm b which extends from the hinge 38 up to a second end d. The second end d of each lever is hinged to the upper surface of the corresponding plate 24 or 26. The pivot pins 38, 40, 38' and 40' are disposed parallel to the floor constituted by the rollers 22 and perpendicular to the axis of rotation XX' of the drum, and are integral with the drum 12. In other words, the levers move in perpendicular planes in the vertical plane of FIG. 1 or FIG. 2. Moreover, as seen, the lower arms a of the levers are disposed in the lateral zones A and B of the drum.

As seen more clearly in FIG. 1, the general direction of arm b of each lever makes an angle f with the corresponding arm a, this angle being less than 90°. The ends c of the arms a of each pair of levers are connected to each other by a rigid bar 42 in the case of the levers 34, 36 and 42' in the case of levers 34', 36'. The end g of the rod of each actuator is hinged to a point of the bar 42 associated with the corresponding pair of levers. The body h of each actuator is pivotally mounted on a support referenced as 48 for the actuator 32 and 50 for the actuator 30.

It will be understood that control of the actuators 30, 32 and the corresponding actuators disposed in the other lateral part of the drum, causes displacement of the corresponding bars 42, 42' and therefore pivoting of the arms a of the pairs of levers about the associated pins 38, 40, 38', 40', which causes simultaneous lowering of the plates 24 and 26 down against the upper surfaces of the stacks of objects 18 and 20. Preferably, the actuators 30, 32 are of the double-acting type which therefore allows the displacements of the end of the rod g to be controlled in both directions, allowing the plates 24 and 26 to be raised and lowered.

It can be seen that, by means of the system described above, use is made of the space available in the lateral zones A and B of the drum, which allows the use of actuators of conventional type having sufficient travel. Moreover, it will be understood that, by the action of the lengths of the arms a and b of the levers, the force is geared down, allowing the lower power actuators to be used. Moreover, it will be understood that the range of movement of the ends d of arms b in the vertical direction is small, this being advantageous as the space available in the upper zone C of the drum is small as described previously.

Referring now to FIGS. 3 to 6, a second embodiment of the system for supporting the objects will be described, in which control of the displacement of the presser plates is achieved by mechanical means.

Figure 3:
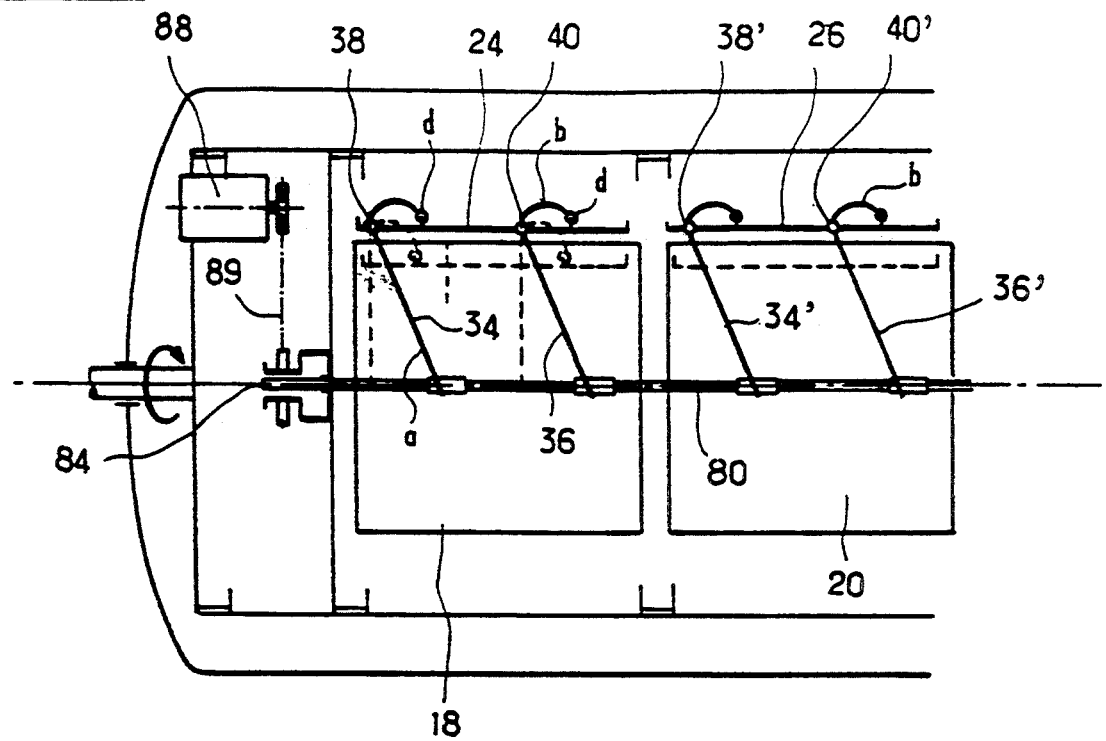
FIG. 3 is a vertical section view of a second embodiment of the support system of the mechanically controlled type.
Figure 4:
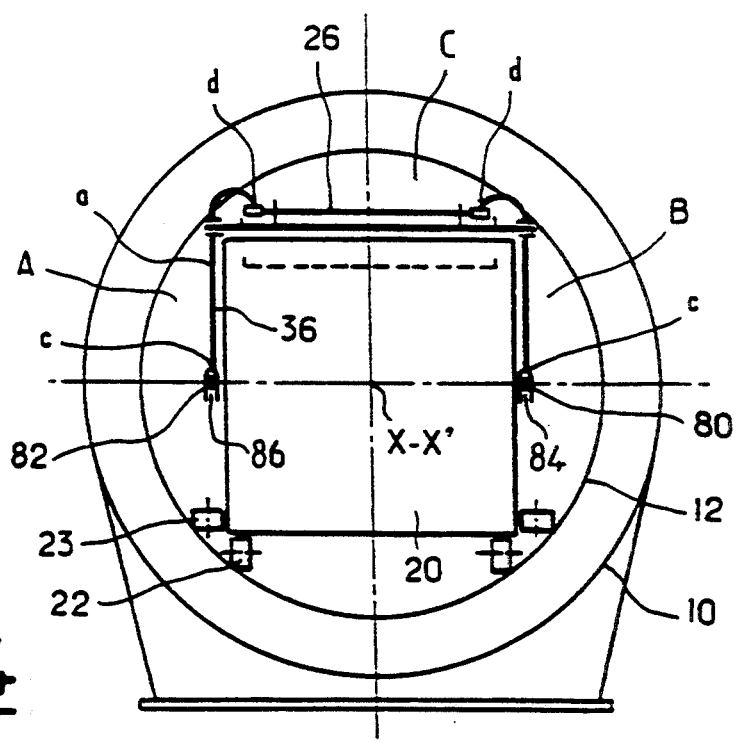
FIG. 4 is a view from the side along the arrow IV of FIG. 3.

In these figures, the same reference numerals are used as in FIGS. 1 and 2 for parts which are common to the two embodiments. As seen in FIG. 3, in this embodiment, the plates 24 and 26 are displaced by pairs of levers 34, 36, 34', 36' identical to those of FIG. 1. Each of these levers comprises two arms a and b which are pivotally mounted about pins 38, 40, 38', 40', these levers being disposed in the lateral zones A and B of the drum, i.e. on either side of the stacks of objects 18 and 20. The ends d of the arms b of the levers are integral with the plates 24 and 26.

Figure 5:
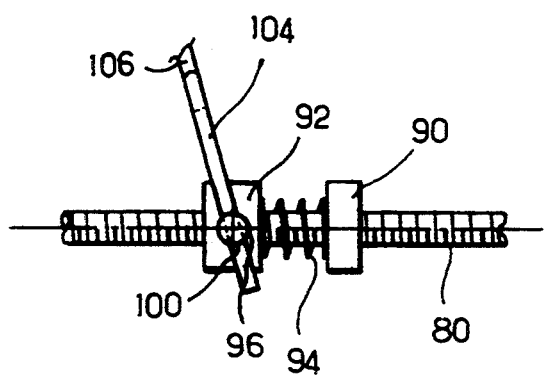
FIGS. 5 and 6 are fragmentary views respectively in elevation and from the front, showing part of the mechanism of FIGS. 3 and 4 which allows the displacement of the means for supporting the stacks of objects.
Figure 6:
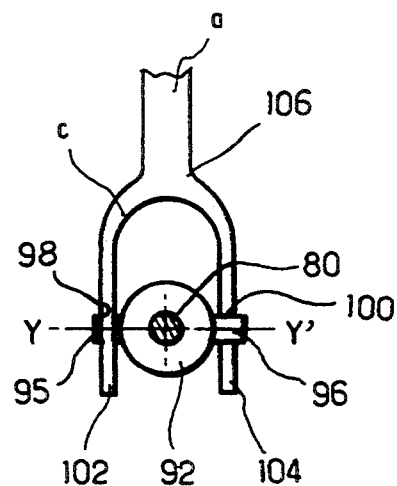

This embodiment differs from that of FIGS. 1 and 2 in the manner in which the displacements of the ends of the arms a of the levers are controlled in order to cause the presser plates 24 and 26 to move up and down. This displacement is controlled by two threaded rods 80 and 82 which are parallel to the pivot axis XX' of the drum and disposed in the lateral regions B and A of the drum respectively. Each threaded rod 80, 82 comprises a respective end 84, 86, which is connected to a drive motor 88 via a reduction gear assembly 89. The threaded rods 80 and 82 are supported by bearings not shown in the figures. For each lever, the threaded rod 80, or 82 respectively, includes a nut 90 as shown in FIGS. 5 and 6. This nut 90 is associated with a ring 92 which engages freely on the threaded rod 80, the nut 90 being connected to the ring 92 by a pre-stressed spring 94. Each ring 92 is provided with two lugs 95 and 96 freely mounted in rotation about an axis YY' perpendicular to the threaded rod 80. The lugs 95 and 96 are provided with drillings 98 and 100 in which the limbs 102 and 104 of a yoke 106 can freely engage, the yoke constituting the end c of the arm a of each lever 34, 36, 34', 36'. Rotation of the rod 80 causes corresponding displacement of the nut 90. This in turn transmits this displacement to the ring 92 via the spring 94. This displacement of the ring 92 itself causes the arm a of the associated lever to pivot in a suitable direction, with consequent displacement of the presser plate 24 or 26. It will be understood that the system constituted by the lugs 98, 94 and 96 in which the ends 102 and 104 of the yoke are freely engaged effectively allows the levers to pivot without the introduction of constraints. The same is true for the threaded rod 82 and the pairs of levers disposed on the other side of the stacks of objects.

It will also be understood that the connection of the driving nut 90 to the driven ring 92 via the spring 94 allows a certain de-coupling of the respective pivoting movements of the levers 34, 36, 34', 36', which therefore allows the position at which the plates 24, 26 are supported to be adapted to the effective height of the stacks of objects 18, 20. It will also be understood that each lever in a single pair, for example levers 34 and 36, is also driven via the resilient systems 94, which ensures the plate is correctly pressed even if the stack of objects is not of uniformly even height.

It follows from the preceding description that the control of presser plates which is displaced to the lateral parts of the drum, on either side of the stacks of objects, has numerous advantages compared with the known solutions in which the pressing means are disposed at the top of the drum in its mid-plane. The stresses caused by the pressing of the plates are conveyed directly to the bottom part of the drum instead of being conveyed to the top of the drum. Releasing space in the top of the drum above the stacks of objects makes it easier to spray the objects when the autoclave is functioning in "static" mode. The pressing forces applied to the plates are applied to the four corners of the plates, which tends to equalize the stresses. Finally, in the case where control is via actuators, conventional actuators with standard diameter and travel can be used.

We claim:

1. A system for supporting at least one stack of objects inside a rotating drum, the system comprising:
   at least one presser plate for application against a top part of a stack of objects inside a rotating drum having a rotation axis, the drum including a floor to receive the stack; and
   means for displacing said plate so as to apply said plate against the stack, said displacement means comprising:
      at least one member forming a lever disposed on at least one side of the stack, and pivotally mounted about a pin secured to the drum, parallel to the floor and perpendicular to the axis of rotation of the drum; and
      means for controlling pivoting of said lever about the pin, said control means also being disposed on one side of the stack, a first end of said lever being driven by said control means and a second end of said lever being secured to the stack, a displacement of said first end of said lever in a first direction causing said second end of said lever to approach said plate, whereby said plate is applied against the top end of the stack.

2. A system for supporting a plurality of stacks of objects inside a rotating drum, the system comprising:
   a plurality of presser plates for application against top parts of a plurality of stacks of objects inside a rotating drum having a rotation axis, the drum including a floor to receive the stacks; and
   means for displacing said plates so as to apply said plates against the stacks, said displacement means comprising:
      for each of the stacks, two pairs of identical levers, each pair being disposed on one side of each of the stacks, respectively, and pivotally mounted about pins secured to the drum, parallel to the floor and perpendicular to the axis of rotation of the drum; and
      means for controlling pivoting of said pairs of levers about the pins, said control means also being disposed on one side of the stacks, a first end of each of said levers being driven by said control means and a second end of each of said levers being secured to the stacks, displacements of said first ends of said levers in a first direction causing said second ends of said levers to approach said plates, said control means applying to said first ends of each of said pairs of levers a displacement which is independent of that which is applied to another pair, whereby said plates are applied against the top ends of the stacks.

3. The system according to claim 2, wherein each of said levers comprises a first arm and a bent second arm disposed on either side of its pivot pin, an angle f between a segment joining the pivot pin to said first end of each of said levers and a segment joining the pivot pin to said second end of each of said levers being less than 90°.

4. The system according to claim 2, wherein said means for controlling pivoting comprise an actuator having a rod with a free end connected to said first end of said lever.

5. The system according to claim 4, wherein said means for controlling pivoting further comprise a bar connecting together said first ends of said levers of a single pair, said bar being connected to said free end of said rod of said actuator.

6. The system according to claim 2, wherein said first end of each of said levers arranged on a same side of the stacks of objects is mechanically connected to a part which is movable in translation parallel to the axis of rotation of the drum, via said control means.

7. The system according to claim 6, wherein said first end of each of said levers is connected to said part by a resilient system which is deformable along a direction of movement of said part.

8. The system according to claim 6, wherein each part is a nut co-operating with a threaded rod disposed parallel to the axis of rotation of the drum, all the nuts disposed on the same side of the stacks of objects co-operating with the same threaded rod.

9. The system according to claim 3, wherein said means for controlling pivoting comprise an actuator having a rod with a free end connected to said first end of said lever.

10. The system according to claim 9, wherein said means for controlling pivoting further comprise a bar connecting together said first ends of said levers of a single pair, said bar being connected to said free end of said rod of said actuator.

11. The system according to clam 3, wherein said first end of each of said levers arranged on a same side of the stacks of objects is mechanically connected to a part which is movable in translation parallel to the axis of rotation of the drum, via said control means.

12. The system according to claim 11, wherein said first end of each of said levers is connected to said part by a resilient system which is deformable along a direction of movement of said part.

13. The system according to claim 11, wherein each part is a nut co-operating with a threaded rod disposed parallel to the axis of rotation of the drum, all the nuts disposed on the same side of the stacks of objects co-operating with the same threaded rod.

* * * * *